United States Patent

Somekh

[11] 3,966,589
[45] June 29, 1976

[54] PROCESS FOR THE SEPARATION OF AROMATIC HYDROCARBONS FROM A MIXED HYDROCARBON FEEDSTOCK

[75] Inventor: George Solomon Somekh, New Rochelle, N.Y.

[73] Assignee: Union Carbide Corporation, New York, N.Y.

[22] Filed: Mar. 17, 1975

[21] Appl. No.: 559,077

Related U.S. Application Data

[63] Continuation-in-part of Ser. No. 439,709, Feb. 5, 1974.

[52] U.S. Cl. .......................... 208/321; 260/674 SE
[51] Int. Cl.² .................................... C10G 21/28
[58] Field of Search ................ 208/321; 260/674 SE

[56] References Cited
UNITED STATES PATENTS

| | | | |
|---|---|---|---|
| 3,551,327 | 12/1970 | Kelly et al. | 208/321 |
| 3,714,033 | 1/1973 | Somekh et al. | 260/674 SE |

*Primary Examiner*—Herbert Levine
*Attorney, Agent, or Firm*—Saul R. Bresch; Alfred D. Lobo

[57] ABSTRACT

A continuous solvent extraction-steam distillation process for the recovery of aromatic hydrocarbons having boiling points in the range of about 80°C. to about 175°C. from a feedstock containing aliphatic hydrocarbons and said aromatic hydrocarbons comprising the following steps:

a. introducing the feedstock into an extraction zone at about the midpoint thereof;
b. introducing a mixture of water and solvent into the extraction zone at about the top of said extraction zone, said solvent being a water-miscible organic liquid having a boiling point of at least about 200°C.;
c. introducing reflux hydrocarbons into the extraction zone at about the bottom thereof;
d. contacting the feedstock in the extraction zone with the mixture of water and a solvent, the water phase of step (j), and the reflux hydrocarbons to provide an extract comprising aromatic hydrocarbons, reflux aliphatic hydrocarbons, solvent, and water and a raffinate comprising essentially aliphatic hydrocarbons;
e. contacting the extract with steam in a distillation zone to provide an overhead distillate comprising a reflux hydrocarbons phase and a water phase, a side cut distillate comprising an aromatic hydrocarbons phase and a water phase, and bottom comprising a mixture of solvent and water;
f. contacting the raffinate with the water phase of step (g) to provide a raffinate aliphatic hydrocarbons phase and a water phase;
g. contacting the raffinate aliphatic hydrocarbons phase of step (f) with the water phase of the side cut distillate to provide a raffinate aliphatic hydrocarbons phase and a water phase;
h. contacting the water phase of the overhead distillate with an aromatic hydrocarbons stream containing at least 95 percent aromatic hydrocarbons, the amount of said stream being in the range of about 0.1 percent to about 5 percent by weight of the total aromatic hydrocarbons in the feedstock, to form an aromatic hydrocarbons phase and a water phase;
i. contacting the aromatic hydrocarbons phase of the side-cut distillate with the water phase of (h) to form an aromatic hydrocarbons phase and a water phase;
j. recycling the water phase of step (f) to the extraction zone at about the midpoint thereof;
k. recycling the water phase of step (i) to the distillation zone where said water phase is essentially converted to steam;
l. recycling the reflux hydrocarbons phase of the overhead distillate and the bottoms of step (e) to the extraction zone to provide, respectively, reflux hydrocarbons for step (c) and mixture of water and solvent, for step (b); and
m. recovering the aromatic hydrocarbons phase of step (i) and the raffinate aliphatic hydrocarbons phase of step (g).

13 Claims, 1 Drawing Figure

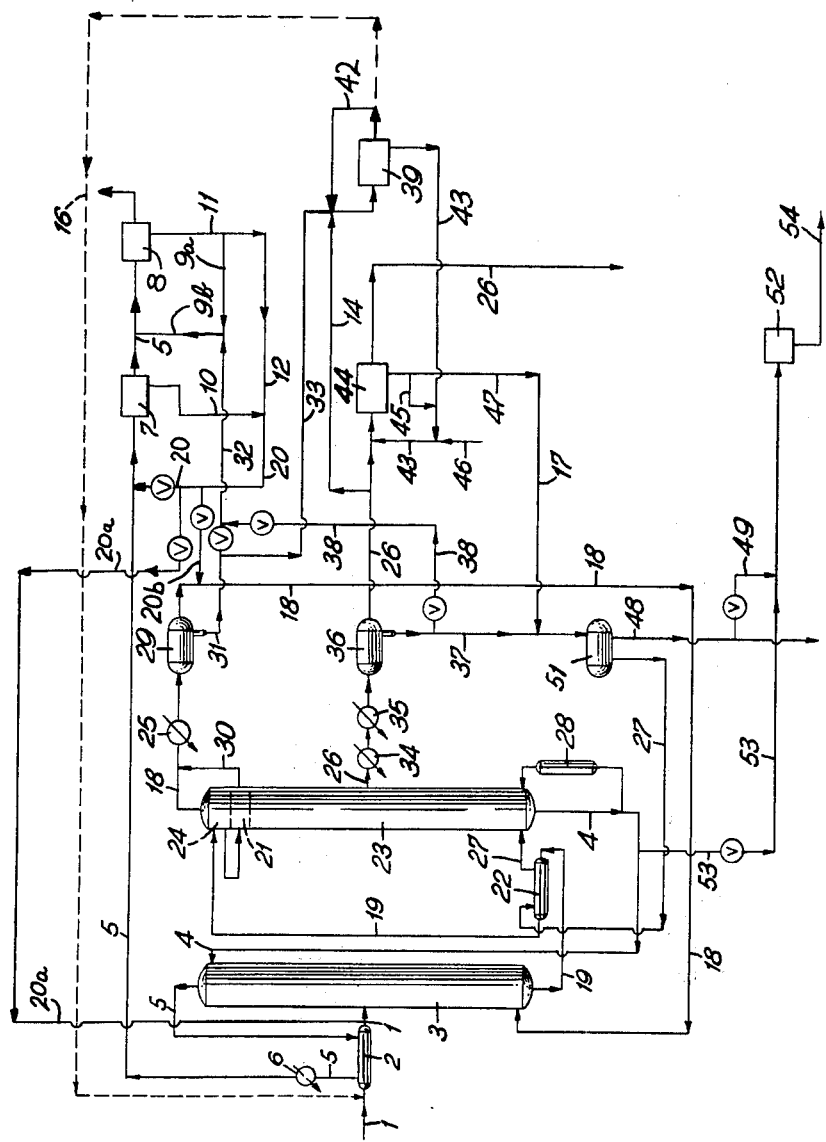

PROCESS FOR THE SEPARATION OF AROMATIC HYDROCARBONS FROM A MIXED HYDROCARBON FEEDSTOCK

This application is a continuation-in-part of application Ser. No. 439,709 filed on Feb. 5, 1974.

FIELD OF THE INVENTION

This invention relates to an improvement in a process for the separation of aromatic hydrocarbons from a mixed hydrocarbon feedstock and, more particularly, to the recovery of high purity aromatic hydrocarbons in high yields while making efficient use of process components.

DESCRIPTION OF THE PRIOR ART

With the advent of the benzene-toluene-$C_8$ aromatics fraction (known and hereinafter referred to as BTX) as the principal raw material in the manufacture of petrochemicals, outstripping ethylene in this regard, and the increased demand for aromatics as a component in gasoline to increase its octane rating and thus reduce or eliminate the need for lead, which has been under fire as a pollutant, aromatics separation processes availed of in the past have come under close scrutiny with an eye toward improving process economics.

Improved process economics can be translated into, among other things, the use of less apparatus, the lowering of heating requirements, and the more effective use of process components as aids in the separation process.

Various processes have been used for aromatics separations, e.g., (1) a process using an extraction column which sends a glycol solvent/water solution, BTX and reflux to a two step distillation column. The resulting BTX is then redistilled to remove water and entrained glycol; (2) a similar process using two distillation columns, BTX and water being distilled in the second column; (3) another similar process using two distillation columns, in the second column of which BTX and glycol are distilled.

Generally, these processes use two separate water circuits. One circuit is the stripping water circuit for removing aromatics from the glycol in the stripper and the other is a water wash circuit. Both water streams are revaporized in these processes. The make-up of the water wash circuit is such that the water first washes raffinate and then is distilled. Unfortunately, distillation does not remove all dissolved and entrained aliphatics from the water and yet it is then used to wash glycol from the aromatics product resulting in decreased product purity. In the stripping water circuit, stripping water from the reflux decanter also contains some aliphatics. Finally, the use of two or more distillation columns is the rule rather than the exception in this type of system.

In one improvement over the foregoing, revaporization is avoided in the water wash circuit; however, a water rectifier is necessary in the stripping water circuit and in another improvement, the water rectifier is avoided, but various untreated water streams are combined to recover the glycol. Although an attempt is made in both improvements to displace aliphatics with aromatics in the process water, it is apparent that aliphatics are necessarily present in the final product thus reducing purity.

In sum, all of the processes mentioned heretofore, while viable commercially, have not succeeded in optimizing process economics together with purity.

Great strides have been made in such optimization and in obtaining high purity benzene; as, for example, in U.S. Pat. No. 3,714,033; however, processes which improve process economics, obtain high purity benzene, and, further, achieve higher toluene and xylene purities are still being sought after.

SUMMARY OF THE INVENTION

An object of this invention, therefore, is to provide an improvement in a process for the separation of aromatic hydrocarbons from a mixed hydrocarbon feedstock in which a solvent-water composition is utilized whereby aromatics are recovered in high purity using a minimum of apparatus and heat and making more effective use of process components.

Other objects and advantages will become apparent hereinafter.

According to the present invention, high purity aromatic hydrocarbons are effectively recovered using minimal apparatus and heat by a continuous solvent extraction - steam distillation process for the recovery of aromatic hydrocarbons having boiling points in the range of about 80°C. to about 175°C. from a feedstock containing aliphatic hydrocarbons and said aromatic hydrocarbons comprising the following steps:

a. introducing the feedstock into an extraction zone at about the midpoint thereof;

b. introducing a mixture of water and solvent into the extraction zone at about the top of said extraction zone, said solvent being a water-miscible organic liquid having a boiling point of at least about 200°C.;

c. introducing reflux hydrocarbons into the extraction zone at about the bottom thereof;

d. contacting the feedstock in the extraction zone with the mixture of water and a solvent, the water phase of step (j), and the reflux hydrocarbons to provide an extract comprising aromatic hydrocarbons, reflux aliphatic hydrocarbons, solvent, and water and a raffinate comprising essentially aliphatic hydrocarbons;

e. contacting the extract with steam in a distillation zone to provide an overhead distillate comprising a reflux hydrocarbons phase and a water phase, a side cut distillate comprising an aromatics hydrocarbons phase and a water phase, and bottoms comprising a mixture of solvent and water; f. contacting the raffinate with the water phase of step (g) to provide a raffinate aliphatic hydrocarbons phase and a water phase;

g. contacting the raffinate aliphatic hydrocarbons of step (f) with the water phase of the side cut distillate to provide a raffinate aliphatic hydrocarbons phase and a water phase;

h. contacting the water phase of the overhead distillate with an aromatic hydrocarbons stream containing at least 95 percent aromatic hydrocarbons, the amount of said stream being in the range of about 0.1 percent to about 5 percent by weight of the total aromatic hydrocarbons in the feedstock to form an aromatic hydrocarbons phase and a water phase;

i. contacting the aromatic hydrocarbons phase of the side-cut distillate with the water phase of (h) to form an aromatic hydrocarbons phase and a water phase;

j. recycling the water phase of step (f) to the extraction zone at about the midpoint thereof;

k. recycling the water phase of step (i) to the distillation zone where said whater phase is essentially converted to steam;

l. recycling the reflux hydrocarbons phase of the overhead distillate and the bottoms of step (e) to the extraction zone to provide, respectively, reflux hydrocarbons for step (c) and mixture of water and solvent for step (b); and m. recovering the aromatic hydrocarbons phase of step (i) and the raffinate aliphatic hydrocarbons phase of step (g).

BRIEF DESCRIPTION OF THE DRAWING

The sole figure is a schematic flow diagram of an illustrative embodiment of the present invention.

DESCRIPTION OF THE PREFERRED EMBODIMENT

As noted above, there is an industrial need for BTX, which is available in high proportion, e.g., greater than 30 percent by weight, in a wide variety of hydrocarbon feedstocks such as reformed gasolines; coke oven light oils; cracked gasolines; and dripolenes, which, after hydrogenation, can contain as much as 70 to 98 percent BTX. These feedstocks also contain both aliphatic and cycloaliphatic hydrocarbons (herein referred to collectively as aliphatic hydrocarbons). Since the individual hydrocarbon compounds which make up these feedstocks are well known, they will not be discussed extensively; however, it can be pointed out that the major components of the feedstocks used herein are hydrocarbons with boiling points ranging from 25°C. to 175°C. including straight-chain and branched-chain paraffins and naphthenes, such as n-heptane, isooctane, and methyl cyclohexane, and aromatics such as BTX.

The BTX fraction can include benzene, toluene, the $C_8$ aromatics including ortho-xylene, meta-xylene, para-xylene, and ethyl benzene, and $C_9$ aromatics which, if present at all, appear in the smallest proportion in relation to the other components.

The solvents used in subject process are, as described above, water-miscible organic liquids (at process temperatures) having a boiling point of at least about 200°C. and having a decomposition temperature of at least about 225°C. The term "water-miscible" includes those solvents which are completely miscible over a wide range of temperatures and those solvents which have a high partial miscibility at room temperature since the latter are usually completely miscible at process temperatures. The solvents are also polar and are generally comprised of carbon, hydrogen and oxygen with some exceptions. Examples of solvents which may be used in the process of this invention are dipropylene glycol, tripropylene glycol, ethylene glycol, diethylene glycol, diethylene glycol monomethyl ether, diethylene glycol monoethyl ether, sulfolane, N-methyl-2-pyrrolidone, triethylene glycol, tetraethylene glycol, acetamide, diethylenetriamine, triethylenetetramine, diethanolamine, para-cresol, meta-cresol, and mixtures thereof. The preferred group of solvents is the polyalkylene glycols and the preferred solvent is tetraethylene glycol.

The apparatus used in the process both for the main extraction and the distillation is conventional, e.g., an extraction column of the multistage reciprocating type containing a plurality of perforated plates centrally mounted on a vertical shaft driven by a motor in an oscillatory manner can be used as well as columns containing pumps with settling zones, sieve trays with upcomers, or even a hollow tube while the distillation can be conducted in a packed or bubble plate fractionating column. Countercurrent flows are utilized in both extraction and distillation columns.

Heat exchangers, decanters, reservoir and solvent regenerator are also conventional as well as various extractors other than the main extractor. These other extractors are preferably single stage mixer-settlers, but can be any of the well known types.

The solvent is used as an aqueous solution thereof and in the case, e.g. of tetraethylene glycol, it usually contains about 4 percent to about 6 percent by weight of water based on the combined weight of the solvent and water and preferably contains water in an amount of about 4.5 percent to about 5 percent by weight. Generally, however, the aqueous solutions contain about 1 to about 8 percent water and preferably about 2 to about 5 percent. This aqueous solution is referred to hereafter in some instances as a solvent-water mixture. In this particular process, the foregoing amounts of water are those used initially and those that will appear in the still bottoms and the upper portion of the extractor, i.e., above the midpoint or feed-point. It is well known that these amounts of water can be adjusted by adjusting the temperature and pressure at the bottom of the still (shown in the drawing as stripper 23). The amounts of water in the lower portion of the extractor, i.e., below the midpoint, will be discussed hereinafter.

Generally, to accomplish the extraction, the ratio of solvent (exclusive of water) to feedstock in the extractor is in the range of about 4 to about 8 parts by weight of solvent to one part by weight of feedstock. This broad range can be expanded upon where non-preferred solvents are used. A broad range of about 3 to about 12 parts by weight of solvent to one part by weight of feedstock and a preferred range of about 5 parts to about 7 parts of solvent per part of feedstock can be used successfully for the solvent of preference and other like solvents. In final analysis, however, the ratio is selected by the technician based on experience with the particular feedstock and depends in part upon whether high recovery or high purity is being emphasized, although the instant process will improve purity in any case.

The reflux to the extraction zone is generally made up of about 20 percent to about 50 percent by weight aliphatics having from 5 to 7 carbon atoms and about 50 percent to about 80 percent by weight aromatics, both based on the total weight of the reflux. The ratio of reflux to feedstock in the extraction zone is, generally, maintained in the range of about 0.5 to about 1.5 parts by weight of reflux to one part by weight of feedstock and preferably about 0.5 to about 1.0 parts by weight of reflux to one part by weight of feedstock, but, again, is selected by the technician just as the ratio of solvent to feedstock. The reflux aliphatics pass into the extract rather than being taken overhead with the raffinate and are recycled to the extractor from the reflux decanter as will be seen hereinafter.

The temperature in the extraction zone is maintained in the range of about 100°C. to about 200°C. and is preferably in the range of about 130°C. to about 180°C., especially for the solvent of preference.

The pressure in the extraction zone is maintained in the range of about 75 psig to about 200 psig. As is well known in the art, however, one selected pressure is not maintained throughout the extraction zone, but, rather, a high pressure within the stated range is present at the bottom of the zone and a low pressure again within the stated range is present at the top of the zone with an intermediate pressure in the middle of the zone. The pressures in the zone depend on the design of the equipment and the temperature, both of which are adjusted to maintain the pressure within the stated range.

The temperature at the top of the distillation zone, which, in terms of the apparatus used, may be referred to as a distillation column or stripper, is at the boiling point of the mixture of aromatics present in the zone while the temperature at the bottom of the stripper is generally in the range of about 135°C. to about 200°C.

The pressure at the top of the stripper, an upper flash zone in this case, is in the range of about 20 psig to about 35 psig. In a lower flash zone just beneath the upper flash zone and connected thereto, the pressure is in the range of about 10 psig to about 20 psig and is about 10 or 15 psig lower than the pressure in the upper flash zone. The pressure in the rest of the distillation zone is maintained in the range of about 5 psig to about 30 psig with some variation throughout the zone.

The steam brought into the bottom of the distillation zone enters at a temperature of about 100°C. to about 150°C. and is under a pressure of about 10 psig to about 25 psig. The total water present in the distillation column is essentially in vapor form and is generally in the range of about 0.1 parts to about 0.5 parts by weight of water to one part by weight of aromatics in the zone and preferably in the range of about 0.1 parts to about 0.3 parts by weight of water to one part by weight of aromatics. The water used for the steam may be called stripping water. A small amount of water is present in liquid form in the distillation zone dissolved in the solvent.

Referring to the drawing:

The feedstock is introduced through line 1 into heat exchanger 2 where it is preheated to a temperature in the range of about 50°C. to about 100°C. It then continues through line 1 to enter extractor 3 at about the middle tray thereof. An aqueous solvent solution having a temperature in the range of about 135°C. to about 200°C. enters at the top tray of extractor 3 through line 4 and percolates down the column removing aromatics from the feedstock.

The raffinate, essentially free of aromatics, leaves the top of the column through heat exchanger 2 where it is used to preheat the feedstock and is cooled in turn to a temperature in the range of 75°C. to about 125°C. The raffinate comprises about 95 percent to about 98 percent by weight aliphatics, about 1 percent to about 3 percent by weight dissolved and entrained solvent, and about 0 percent to about 3 percent by weight aromatics. The raffinate then passes through cooler 6 where it is further cooled to about 25°C. to about 50°C. and proceeds along line 5 to mixer-settler 7 where it is contacted with a portion of the water phase coming from mixer-settler 8 via lines 11, 12, 20, and 5 combined with a recirculated portion of its own water phase, which passes through lines 10, 20, and 5. The first stage raffinate wash takes place in mixer-settler 8 and the second stage raffinate wash takes place in mixer-settler 7. In both mixer-settlers 7 and 8 a raffinate aliphatic hydrocarbons phase and a water phase are formed, each water phase being contaminated with aliphatics. It should be pointed out that the mixer-settler is represented by a box to denote a zone. In fact, a mixer-settler is two pieces of apparatus, the mixer in which the mixing is accomplished and the settler in which the settling is accomplished. Single stage mixer-settlers are preferred here, but other conventional types of extractor can be used.

It also should be noted that the "phase" is named after its main component, which is present in the phase in an amount of at least 50 percent by weight and, in most cases, in an amount of at least 90% by weight.

The aliphatic hydrocarbons phase leaving mixer-settler 7 via line 5 can still be referred to as the raffinate and now contains about 96 percent to about 99 percent by weight aliphatics, about 0 percent to about 1 percent by weight dissolved and entrained solvent, and about 0 percent to about 3 percent by weight aromatics. The water phase, on the other hand, contains about 48 percent to about 84 percent by weight water, about 15 percent to about 50 percent by weight solvent, and about 1 percent to about 2 percent by weight aliphatics.

The raffinate continues overhead through line 5 into mixer-settler 8.

The balance, generally a major proportion or more than 50% by weight, of the combined water phases passing through line 20 is preferably sent through line 20a to join line 1 and enter extractor 3 at about its midpoint.

The raffinate wash which takes place in mixer-settler 8 is called the first stage raffinate wash simply because the water used in this wash comes directly from the system whereas the water used in the raffinate wash in mixer-settler 7 comes from mixer-settler 8. See above. These washes are counter-current. It should be noted that a portion of the water phase from mixer-settler 8 is optionally recirculated to mixer-settler 8 via lines 11, 9a, 9b, and 5. Aside from the recirculated water phase, the water used in mixer-settler 8 is preferably obtained from aromatics decanter 36 via lines 37, 38, 32, 9b, and 5, but can be alternatively obtained from reflux decanter 29 via lines 31, 32, 9b, and 5. The aromatics decanter 36 source is used, e.g., where the feed is a high aromatics one and the pentanes present in the feed reduce the water flow from reflux decanter 29. The technician has to make this choice depending on the availability of water from the mentioned sources. In some cases both sources can be used. In any event, it is understood that initial water may be introduced from outside sources.

Another option open to the technician and also dependent on the composition of the feed is whether a two stage raffinate wash or a single stage raffinate wash is to be used. In most cases the two stage raffinate wash described here is to be preferred. The single stage raffinate wash is accomplished, however, by eliminating mixer-settler 7, line 10, and line 9b. Recirculation to mixer-settler 8 would then follow the path along lines 11, 12, 20, and 5. the single stage wash is generally effected in cases where there is a small raffinate, e.g., in dripolenes.

The components in mixer-settler 8 separate into an aliphatic hydrocarbons phase (still called the raffinate) which is essentially free of solvent and water and contains about 97 percent to about 100 percent by weight aliphatics and about 0 percent to about 3 percent by weight aromatics, and a raffinate water phase as bottoms which contains about 95 percent to about 98 percent by weight water, about 0.1 percent to about 3.0 percent by weight solvent, and about 1 percent to about 2 percent by weight aliphatics. The separation in mixer-settler 7 is about the same, but the raffinate still has some solvent and water so the percentages of aliphatics has to be revised downward.

As pointed out, part of the raffinate water phase can optionally be recirculated through the mixer-settler from which it came. In the case of mixer-settler 8, the recirculation would take place along lines 11, 9a, 9b, and 5. In the case of mixer-settler 7, the recirculation would take place along lines 10, 20, and 5. This recirculation is conventional with a mixer-settler arrangement, but may not be advantageous with other types of extractors.

The balance of the combined raffinate water phases which was taken along lines 20, 20a, and 1 to enter extractor 3 dissolves in the rich solvent passing down the extractor past the midpoint and passes into the lower half of the extractor column. This additional water in the lower half of the extractor causes aliphatics to come out of the extract solution by displacement thus purifying the aromatics having a particular effect on toulene and xylene purities. The lower water content at the top of the extractor increases solvency in the top of the extractor for aliphatics while at the bottom solvency is reduced and selectivity for aromatics increased. It was noted above that the water in the upper half of the extractor is used in the amount of about 4 to about 6 percent by weight based on the combined weight of the solvent and water and preferably about 4.5 to about 5 percent. The water in the lower half of the extractor is about 0.25 to about 1.5 percent above that in the upper half of the extractor and is preferably about 0.75 to about 1.25 percent above. The percentages here are again based on the total weight of the mixture of solvent and water in the extraction zone.

If there is insufficient water in the raffinate water phase, or anywhere in the system, outside water can, of course, be used; however, side stream water via lines 37, 38, 32, 9b and 5 can be and is preferably used to make up any lack in the raffinate water phase. The use of this side stream water does reduce the amount of stripping water available, but this can be simply taken care of by raising the bottoms temperature of stripper 23. The recycle of the raffinate water phase to the midpoint of the extractor also permits the reduction of the solvent to feedstock ratio referred to above thus providing a saving in solvent.

Another option is the addition of water to the bottom of extractor 3 via lines 20b and 18. This water can be all or part of the balance of the combined raffinate water phases which, as noted above, was preferably sent along line 20a. While not increasing the water content of the solvent solution below the feed point, this option does result in the oiling out of an additional hydrocarbon layer at the bottom of extractor 3. This hydrocarbon layer passes up the lower half of extractor 3 and increases the purification in that zone.

It has been noted above that the aqueous solvent percolates down extractor 3 carrying with it the aromatics and joining the raffinate water phase. In the lower half of extractor 3, the solvent solution of aromatics comes into countercurrent contact with a reflux liquid, which enters extractor 3 below the bottom tray along line 18. The reflux percolates up the lower half of extractor 3 progressively dissolving in and purifying the solvent solution of aromatics. The solution which is formed, i.e., the extract, comprises about 5 percent to about 10 percent by weight feedstock aromatics, about 3 percent to about 6 percent by weight water, about 75 percent to about 85 percent by weight solvent, about 4 percent to about 8 percent by weight reflux aromatics, and about 3 percent to about 6 percent by weight reflux aliphatics, all based on the total weight of the extract.

The extract leaves the bottom of extractor 3 through line 19 and passes through heat exchanger 22 where it is cooled to a temperature in the range of about 100°C to about 140°C. The extract proceeds along line 19 and enters stripper 23, the distillation zone, at upper flash chamber 24, which, as noted heretofore, is at a lower pressure than the extractor. Part of the extract flashes on entering the flash chamber and is taken overhead through line 18 in vapor form. Another part of the extract passes as a liquid into lower flash chamber 21, which is operated at an even lower pressure and further flashing occurs. It should be noted that flashing is minimized in the present process. The flashed vapors join the fractionated vapors and pass through line 30 to join the vapors passing through line 18. The balance of the extract (at least about 80 percent by weight) percolates down the column into the fractionation zone where it comes into countercurrent contact with the stripping vapors, i.e., steam, and more vapors are generated. A part of the vapor rises to the top of the column and mixes with the flashed vapors in flash chamber 21 as noted. The overhead distillate comprises about 40 to about 75 percent by weight aromatics, about 20 to about 40 percent aliphatics, about 2 percent to about 10 percent by weight water, and about 0 percent to about 5 percent by weight solvent, all based on the total weight of the overhead distillate.

After the aqueous solvent descends about halfway down the column, it becomes essentially free of aliphatics. At this point, a vapor side-stream distillate is removed through line 26. The side-stream distillate is comprised of about 65 to about 90 percent by weight aromatics, about 10 to about 30 percent by weight water, and about 1 percent to about 10 percent by weight of solvent, based on the total weight of the side-stream distillate.

The bulk of the solvent and water solution, an amount equal to over 90 percent by weight of the solvent and water entering stripper 23 through line 19, leaves the bottom of stripper 23 through line 4. A portion of this solution is diverted into reboiler 28 and returns as a vapor to a point below the bottom tray of stripper 23 to provide most of the stripper's heating requirements. The balance of the water and solvent solution is recycled to the top tray of extractor 3 through line 4. Recycled stripping water containing some dissolved solvent enters stripper 23 through line 27 from water reservoir 51 after essentially all of it is converted in heat exchanger 22 to steam. Returning to the overhead distillate mentioned heretofore, such overhead distillate is a combination of flashed vapors and fractionated vapors having the aforementioned composition. This overhead distillate is also known as a reflux distillate. The vapor is first condensed and cooled to between about 38°C. and 94°C. in reflux condenser 25. The condensate then passes into reflux decanter 29 where a reflux hydrocarbons phase is decanted from a water phase. The reflux hydrocarbons phase comprises about 20 to 50 percent by weight aliphatics having from 5 to 7 carbon atoms, and about 50 to about 80 percent by weight aromatics and is recycled as reflux through line 18 to extractor 3 as previously described.

The water phase contains about 95 to about 99 percent by weight water, about 0 to about 5 percent by weight solvent, and about 0.1 to about 0.5 percent by weight aliphatics. It passes through line 31 and may be split into two streams, lines 32 and 33, a raffinate wash stream and an aromatics wash stream, respectively, depending, as noted above, on the amount of water available. The preferred mode of operation, however, is to use the reflux distillate water phase for the aromatics wash and the side cut distillate water phase for the raffinate wash.

As noted heretofore, the side-stream distillate is withdrawn in vapor form from stripper 23 through line 26 and condensed in aromatics condenser 34 and further cooled to a temperature in the range of about 25°C. to about 50°C. in cooler 35, which can be a heat exchanger or other type of cooling device. The condensate then passes into aromatics decanter 36 where an aromatic hydrocarbons phase containing about 99.8 to about 99.9 percent by weight aromatics, and about 0.1 to about 0.2 percent by weight solvent and a water phase containing about 90 percent to about 98 percent by weight water, about 2 percent to about 10 percent by weight solvent, and about 0.1 percent to about 0.5 percent by weight aromatics are formed. The water phase may pass through line 37 to water reservoir 51. Preferably, however, all or part of the water phase is directed through valved line 38 to join line 32 for use as raffinate wash.

The aromatic hydrocarbons phase proceeds from decanter 36 through line 26 along which an aromatics slipstream is taken through line 14 to wash water coming from reflux decanter 29 along line 33. The aromatics slipstream at is source is an essentially pure stream of aromatics, i.e., having a purity of at least 95 percent by weight, or in other words, at least 95 percent by weight of the slipstream is aromatic hydrocarbons. The purity of the slipstream is preferably about 98 percent and for optimum performance, i.e., to obtain the highest purity product, about 99 percent. It is called a slipstream or sidestream because the amount of aromatics fed into the water phase passing through line 33 is very small. The amount of slipstream aromatic hydrocarbons used in the process is in the range of about 0.1 percent to about 5 percent by weight of the aromatic hydrocarbons in the feedstock and is preferably in the range of about 0.5 percent to about 2.0 percent by weight of such aromatic hydrocarbons. The slipstream washes the water in extractor 39 to remove the small amount of aliphatics, which is so detrimental to the efficiency of the process. This aromatics slipstream is then, preferably, sent along line 16 to line 1 where it is reintroduced into the feedstock and passes into the system once more, or, alternatively, it is removed from the system.

In practice, the weight of the total aromatics is determined by analysis of a sample portion of the feedstock. Aromatics added, e.g., as slipstream, during the process cycle are included in the determination.

The slipstream can, alternatively, be obtained from another source such as the overhead product of a benzene fractionating column, which is not shown in the drawing, or from a source completely removed from the system. As long as the slipstream has the previously noted high aromatics content, it will be satisfactory in this process.

The combined streams of lines 33 and 14 proceed into wash extractor 39, which can be a single stage mixer-settler or other form of extractor. Where a mixer-settler is used, it is advantageous to use an aromatics recycle which passes along line 42 and joins lines 33 and 14 returning to wash extractor 39. The slipstream, now containing a small amount of aliphatics, passes from wash extractor 39 into line 16 as discussed previously.

Reflux water, now essentially free of aliphatics, is withdrawn from wash extractor 39 and proceeds along line 43, which joins line 26, and passes into aromatics extractor 44, which can be a single stage mixer-settler or other type of extractor. This reflux water, along with water recycled from the settling zone in the case of a mixer-settler via line 45, which joins line 43, and process makeup water from line 46 (source not shown) contacts the aromatic product proceeding along line 26 into aromatics extractor 44 and recovers essentially all of the small amount of solvent remaining in the aromatics. This water with solvent then proceeds along line 47 to join line 17, which joins line 37 and enters water reservoir 51. This water can, optionally, be sent from line 17 to line 38 (connecting line and valve not shown) for use in the raffinate wash. High purity aromatic product is withdrawn from the process through line 26.

There is a provision for the removal of certain impurities, which may include some aliphatics, of a type which can build up in the system and affect it in a deleterious manner. This is accomplished by taking a small purge of the water circuit. To accomplish this purge, water is withdrawn from any of the decanters and discarded periodically or continuously. One such purge can be accomplished through line 48. It is found that only a small proportion of the solvent is lost by such a purge; however, this solvent can be recovered if desired. The water purge stream can be in the range of about 0.25 percent to about 2.0 percent by weight of the total water in the system and is preferably in the range of about 0.5 percent to about 1.0 percent by weight of the water in the system.

The total water in the system can be determined easily because the amount of water introduced can be controlled. Allowances must be made for water losses through leakage, entrainment and upsets, however.

Solvent can be recovered from this purge by directing the water through line 49 to join line 53 and enter solvent regenerator 52 where the solvent is separated from low boiling and high boiling inpurities by steam distillation under vacuum. The solvent is recovered and recycled along line 54 to extractor 3 (connection not shown) and the water and impurities discarded.

An alternative wash system can take the following path: the water phase from reflux decanter 29 passes via lines 31 and 33 into wash extractor 39 and then what was referred to above as reflux water passes through line 43 to aromatics extractor 44. This water with solvent proceeds through lines 47 and into line 17 where part of it is sent to line 38 (not shown), the valve between lines 37 and 38 is closed, and the remainder passes into line 37 as noted above. The advantage in this procedure is that the entire water phase from reflux decanter 29 can be used to wash the aromatics and can be used to provide all of the wash water for the raffinate wash thus further reducing solvent losses.

I claim:

1. A continuous solvent extraction-steam distillation process for the recovery of aromatic hydrocarbons having boiling points in the range of about 80°C. to about 175°C. from a feedstock containing aliphatic hydrocarbons and said aromatic hydrocarbons comprising the following steps:

a. introducing the feedstock into an extraction zone at about the midpoint thereof;
b. introducing a mixture of water and solvent into the extraction zone at about the top of said extraction zone, said solvent being a water-miscible organic liquid having a boiling point of at least about 200°C.
c. introducing reflux hydrocarbons into the extraction zone at about the bottom thereof;
d. contacting the feedstock in the extraction zone with the mixture of water and a solvent, the water phase of step (j), and the reflux hydrocarbons to provide an extract comprising aromatic hydrocarbons, reflux aliphatic hydrocarbons, solvent, and water and a raffinate comprising essentially aliphatic hydrocarbons;
e. contacting the extract with steam in a distillation zone to provide an overhead distillate comprising a reflux hydrocarbons phase and a water phase, a side cut distillate comprising an aromatic hydrocarbons phase and a water phase, and bottoms comprising a mixture of solvent and water;
f. contacting the raffinate with the water phase of step (g) to provide a raffinate aliphatic hydrocarbons phase and a water phase;
g. contacting the raffinate aliphatic hydrocarbons phase of step (f) with the water phase of the side cut distillate to provide a raffinate aliphatic hydrocarbons phase and a water phase;
h. contacting the water phase of the overhead distillate with an aromatic hydrocarbons stream containing at least 95 percent aromatic hydrocarbons, the amount of said stream being in the range of about 0.1 percent to about 5 percent by weight of the total aromatic hydrocarbons in the feedstock, to form an aromatic hydrocarbons phase and a water phase;
i. contacting the aromatic hydrocarbons phase of the side-cut distillate with the water phase of (h) to form an aromatic hydrocarbons phase and a water phase;
j. recycling the water phase of step (f) to the extraction zone at about the midpoint thereof;
k. recycling the water phase of step (i) to the distillation zone where said water phase is essentially converted to steam;
l. recycling the reflux hydrocarbons phase of the overhead distillate and the bottoms of step (e) to the extraction zone to provide, respectively, reflux hydrocarbons for step (c) and mixture of water and solvent for step (b); and
m. recovering the aromatic hydrocarbons phase of step (i) and the raffinate aliphatic hydrocarbons phase of step (g).

2. The process of claim 1 wherein the water in the lower half of the extraction zone is about 0.25 percent to about 1.5 percent above that of the water in the upper half of the extraction zone, said percentages based on the total weight of the mixture of solvent and water in the upper half of the extraction zone.

3. The process of claim 2 wherein the water in the lower half of the extraction zone is about 0.75 percent to about 1.25 percent above that of the water in the upper half of the extraction zone.

4. The process of claim 2 wherein the reflux aliphatic hydrocarbons contain from 5 to 7 carbon atoms.

5. The process of claim 4 wherein:
i. the ratio of solvent to feedstock in the extraction zone is in the range of about 3 to about 12 parts by weight of solvent to one part by weight of feedstock;
ii. the amount of water in the upper half of the extraction zone is about 4 percent to about 6 percent by weight based on the weight of the solvent in said zone;
iii. the ratio of reflux to feedstock in the extraction zone is in the range of about 0.5 to about 1.5 parts by weight of reflux to one part by weight of feedstock; and
iv. the ratio of water to aromatic hydrocarbons in the distillation zone is in the range of about 0.1 to about 0.5 part by weight of water to one part by weight of aromatic hydrocarbons in said zone.

6. The process of claim 5 wherein the solvent is a polyalkylene glycol.

7. The process of claim 6 wherein the solvent is tetraethylene glycol.

8. The process defined in claim 5 with the following additional step:
n. recycling the aromatic hydrocarbons phase of step (h) to the extraction zone.

9. A continuous solvent extraction-steam distillation process for the recovery of aromatic hydrocarbons having boiling points in the range of about 80°C. to about 175°C. from a feestock containing aliphatic hydrocarbons and said aromatic hydrocarbons comprising the following steps:

a. introducing the feedstock into an extraction zone at about the midpoint thereof;
b. introducing a mixture of water and solvent into the extraction zone at about the top of said extraction zone, said solvent being a water-miscible organic liquid having a boiling point of at least about 200°C.
c. introducing reflux hydrocarbons into the extraction zone at about the bottom thereof;
d. contacting the feedstock in the extraction zone with the mixture of water and a solvent, the water phase of step (i), and the reflux hydrocarbons to provide an extract comprising aromatic hydrocarbons, reflux aliphatic hydrocarbons, solvent, and water and a raffinate comprising essentially aliphatic hydrocarbons;
e. contacting the extract with steam in a distillation zone to provide an overhead distillate comprising a reflux hydrocarbons phase and a water phase, a side cut distillate comprising an aromatic hydrocarbons phase and a water phase, and bottoms comprising a mixture of solvent and water;
f. contacting the raffinate with the water phase of the side cut distillate to provide a raffinate aliphatic hydrocarbons phase and a water phase;
g. contacting the water phase of the overhead distillate with an aromatic hydrocarbons stream containing at least 95 percent aromatic hydrocarbons, the amount of said stream being in the range of about 0.1 percent to about 5 percent by weight of the total aromatic hydrocarbons in the feedstock, to form an aromatic hydrocarbons and a water phase;
h. contacting the aromatic hydrocarbons phase of the side-cut distillate with the water phase of (g) to form an aromatic hydrocarbons phase and a water phase;

i. recycling the water phase of step (f) to the extraction zone at about the midpoint thereof;

j. recycling the water phase of step (h) to the distillation zone where said water phase is essentially converted to steam;

k. recycling the reflux hydrocarbons phase of the overhead distillate and the bottoms of step (e) to the extraction zone to provide, respectively, reflux hydrocarbons for step (c) and mixture of water and solvent, for step (b); and l. recovering the aromatic hydrocarbons phase of step (h) and the raffinate aliphatic hydrocarbons phase of step (f).

10. The process defined in claim 9 with the following additional step:

m. recycling the aromatic hydrocarbons phase of step (g) to the extraction zone.

11. A continuous solvent extraction-steam distillation process for the recovery of aromatic hydrocarbons having boiling points in the range of about 80°C. to about 175°C. from a feedstock containing aliphatic hydrocarbons and said aromatic hydrocarbons comprising the following steps:

a. introducing the feedstock into an extraction zone at about the midpoint thereof;

b. introducing a mixture of water and solvent into the extraction zone at about the top of said extraction zone, said solvent being a water-miscible organic liquid having a boiling point of at least about 200°C.;

c. introducing reflux hydrocarbons into the extraction zone at about the bottom thereof;

d. contacting the feedstock in the extraction zone with the mixture of water and a solvent, the water phase of step (j), and the reflux hydrocarbons to provide an extract comprising aromatic hydrocarbons, reflux aliphatic hydrocarbons, solvent, and water and a raffinate comprising essentially aliphatic hydrocarbons;

e. contacting the extract with steam in a distillation zone to provide an overhead distillate comprising a reflux hydrocarbons phase and a water phase, a side cut distillate comprising an aromatic hydrocarbons phase and a water phase, and bottoms comprising a mixture of solvent and water;

f. contacting the raffinate with the water phase of step (g) to provide a raffinate aliphatic hydrocarbons phase and a water phase;

g. contacting the raffinate aliphatic hydrocarbons phase of step (f) with the water phase of the side cut distillate to provide a raffinate aliphatic hydrocarbons phase and a water phase;

h. contacting the water phase of the overhead distillate with an aromatic hydrocarbons stream containing at least 95 percent aromatic hydrocarbons, the amount of said stream being in the range of about 0.1 percent to about 5 percent by weight of the total aromatic hydrocarbons in the feed-stock, to form an aromatic hydrocarbons phase and a waterphase;

i. contacting the aromatic hydrocarbons phase of the side-cut distillate with the water phase of (h) to form an aromatic hydrocarbons phase and a water phase;

j. recycling the water phase of step (f) to the extraction zone at about the bottom thereof;

k. recycling the water phase of step (i) to the distillation zone where said water phase is essentially converted to steam;

l. recycling the reflux hydrocarbons phase of the overhead distillate and the bottoms of step (e) to the extraction zone to provide, respectively, reflux hydrocarbons for step (c) and mixture of water and solvent, for step (b); and m. recovering the aromatic hydrocarbons phase of step (i) and the raffinate aliphatic hydrocarbons phase of step (g).

12. A continuous solvent extraction-steam distillation process for the recovery of aromatic hydrocarbons having boiling points in the range of about 80°C. to about 175°C. from a feedstock containing aliphatic hydrocarbons and said aromatic hydrocarbons comprising the following steps:

a. introducing the feedstock into an extraction zone at about the midpoint thereof;

b. introducing a mixture of water and solvent into the extraction zone at about the top of said extraction zone, said solvent being a water-miscible organic liquid having a boiling point of at least about 200°C.;

c. introducing reflux hydrocarbons into the extraction zone at about the bottom thereof;

d. contacting the feedstock in the extraction zone with the mixture of water and a solvent, the water phase of step (k), and the reflux hydrocarbons to provide an extract comprising aromatic hydrocarbons, reflux aliphatic hydrocarbons, solvent, and water and a raffinate comprising essentially aliphatic hydrocarbons;

e. contacting the extract with steam in a distillation zone to provide an overhead distillate comprising a reflux hydrocarbons phase and a water phase, a side cut distillate comprising an aromatic hydrocarbons phase and a water phase, and bottoms comprising a mixture of solvent and water;

f. dividing the water phase of the overhead distillate into first and second streams;

g. contacting the raffinate with the water phase of step (h) to provide a raffinate aliphatic hydrocarbons phase and a water phase;

h. contacting the raffinate aliphatic hydrocarbons phase of step (g) with the first water stream of step (f) to provide a raffinate aliphatic hydrocarbons phase and a water phase;

i. contacting the second stream of the overhead distillate with an aromatic hydrocarbons stream containing at least 95 percent aromatic hydrocarbons, the amount of said stream being in the range of about 0.1 percent to about 5 percent by weight of the total aromatic hydrocarbons in the feedstock, to form an aromatic hydrocarbons phase and a water phase;

j. contacting the aromatic hydrocarbons phase of the side-cut distillate with the water phase of (i) to form an aromatic hydrocarbons phase and a water phase;

k. recycling the water phase of step (g) to the extraction zone at about the midpoint thereof;

l. recycling the water phase of step (j) to the distillation zone where said water phase is essentially converted to steam;

m. recycling the reflux hydrocarbons phase of the overhead distillate and the bottoms of step (e) to the extraction zone to provide, respectively, reflux hydrocarbons for step (c) and mixture of water and solvent, for step (b); and n. recovering the aromatic hydrocarbons phase of step (j) and the raffinate aliphatic hydrocarbons phase of step (h).

13. A continuous solvent extraction-steam distillation process for the recovery of aromatic hydrocarbons having boiling points in the range of about 80°C. to about 175°C. from a feedstock containing aliphatic hydrocarbons and said aromatic hydrocarbons comprising the following steps:

a. introducing the feedstock into an extraction zone at about the midpoint thereof;

b. introducing a mixture of water and solvent into the extraction zone at about the top of said extraction zone, said solvent being a water-miscible organic liquid having a boiling point of at least about 200°C.;

c. introducing reflux hydrocarbons into the extraction zone at about the bottom thereof;

d. contacting the feedstock in the extraction zone with the mixture of water and a solvent, the water phase of step (k), and the reflux hydrocarbons to provide an extract comprising aromatic hydrocarbons, reflux aliphatic hydrocarbons, solvent, and water and a raffinate comprising essentially aliphatic hydrocarbons;

e. contacting the extract with steam in a distillation zone to provide an overhead distillate comprising a reflux hydrocarbons phase and a water phase, a side cut distillate comprising an aromatic hydrocarbons phase and a water phase, and bottoms comprising a mixture of solvent and water;

f. contacting the water phase of the overhead distillate with an aromatic hydrocarbons stream containing at least 95 percent aromatic hydrocarbons, the amount of said stream being in the range of about 0.1 percent to about 5 percent by weight of the total aromatic hydrocarbons in the feedstock, to form an aromatic hydrocarbons phase and a water phase;

g. contacting the aromatic hydrocarbons phase of the side-cut distillate with the water phase of step (f) to form an aromatic hydrocarbons phase and a water phase;

h. dividing the water phase of step (g) into a first stream and a second stream;

i. contacting the raffinate with the water phase of step (j) to provide a raffinate aliphatic hydrocarbons phase and a water phase;

j. contacting the raffinate aliphatic hydrocarbons phase of step (i) with the first stream of step (h) to provide a raffinate aliphatic hydrocarbons phase and a water phase;

k. recycling the water phase of step (i) to the extraction zone at about the midpoint thereof;

l. recycling the second stream of step (h) to the distillation zone where said second stream is essentially converted to steam;

m. recycling the reflux hydrocarbons phase of the overhead distillate and the bottoms of step (e) to the extraction zone to provide, respectively, reflux hydrocarbons for step (c) and mixture of water and solvent for step (b); and n. recovering the aromatic hydrocarbons phase of step (g) and the raffinate aliphatic hydrocarbons phase of step (j).

* * * * *

UNITED STATES PATENT OFFICE
CERTIFICATE OF CORRECTION

Patent No. 3,966,589     Issue Date June 29, 1976

Inventor(s) George Solomon Somekh

It is certified that error appears in the above-identified patent and that said Letters Patent are hereby corrected as shown below:

Cover page, column 1, middle of column, delete "; Alfred D. Lobo"

Signed and Sealed this

Fifteenth Day of February 1977

[SEAL]

Attest:

RUTH C. MASON
*Attesting Officer*

C. MARSHALL DANN
*Commissioner of Patents and Trademarks*